United States Patent
Fujiwara et al.

(10) Patent No.: US 7,414,148 B2
(45) Date of Patent: Aug. 19, 2008

(54) PROCESS FOR PRODUCING ALKOXYCARBONYLFLUOROALKANE SULFONATES

(75) Inventors: Masaki Fujiwara, Iruma-gun (JP); Jonathan Joachim Jodry, Kawagoe (JP); Satoru Narizuka, Saitama (JP)

(73) Assignee: Central Glass Company Limited, Ube-shi (JP)

( * ) Notice: Subject to any disclaimer, the term of this patent is extended or adjusted under 35 U.S.C. 154(b) by 0 days.

(21) Appl. No.: 11/923,197

(22) Filed: Oct. 24, 2007

(65) Prior Publication Data

US 2008/0108846 A1 May 8, 2008

(30) Foreign Application Priority Data

Oct. 24, 2006 (JP) ............... 2006-289191

(51) Int. Cl.
*C07C 309/57* (2006.01)
*C07C 309/19* (2006.01)
(52) U.S. Cl. ....................... 562/100; 562/109
(58) Field of Classification Search ......... 562/100, 562/109
See application file for complete search history.

(56) References Cited

U.S. PATENT DOCUMENTS

| 2,852,554 | A | 9/1958 | England |
| 2002/0102491 | A1 | 8/2002 | Kodama et al. |
| 2003/0194639 | A1 | 10/2003 | Miya et al. |
| 2005/0130060 | A1 | 6/2005 | Kodama et al. |
| 2007/0003871 | A1 | 1/2007 | Kodama et al. |

FOREIGN PATENT DOCUMENTS

| JP | 2002-214774 A | 7/2002 |
| JP | 2004-004561 A | 1/2004 |
| JP | 2004-117959 A | 4/2004 |

OTHER PUBLICATIONS

"Perfluorooctyl Sulfonates; Proposed Significant New Use Rule" dated Oct. 18, 2000 (vol. 65, No. 202) from the U.S. Environmental Protection Agency.

*Primary Examiner*—Paul A Zucker
(74) *Attorney, Agent, or Firm*—Crowell & Moring LLP

(57) ABSTRACT

A process for producing an alkoxycarbonylfluoroalkanesulfonate represented by the formula [1] is provided. This process includes the steps of (a) reacting a halofluoroalkanoate represented by the formula [2], with a sulfinating agent, thereby obtaining an alkoxycarbonylfluoroalkanesulfinate represented by the formula [3]; and (b) reacting the alkoxycarbonylfluoroalkanesulfinate with an oxidizing agent, thereby obtaining the target alkoxycarbonylfluoroalkanesulfonate. Furthermore, it is possible to react the obtained alkoxycarbonylfluoroalkanesulfonate with a monovalent onium salt to conduct a salt exchange, thereby obtaining a alkoxycarbonylfluoroalkanesulfonic acid onium salt represented by the formula [4].

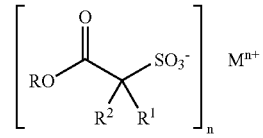

[1]

18 Claims, 1 Drawing Sheet

FIGURE
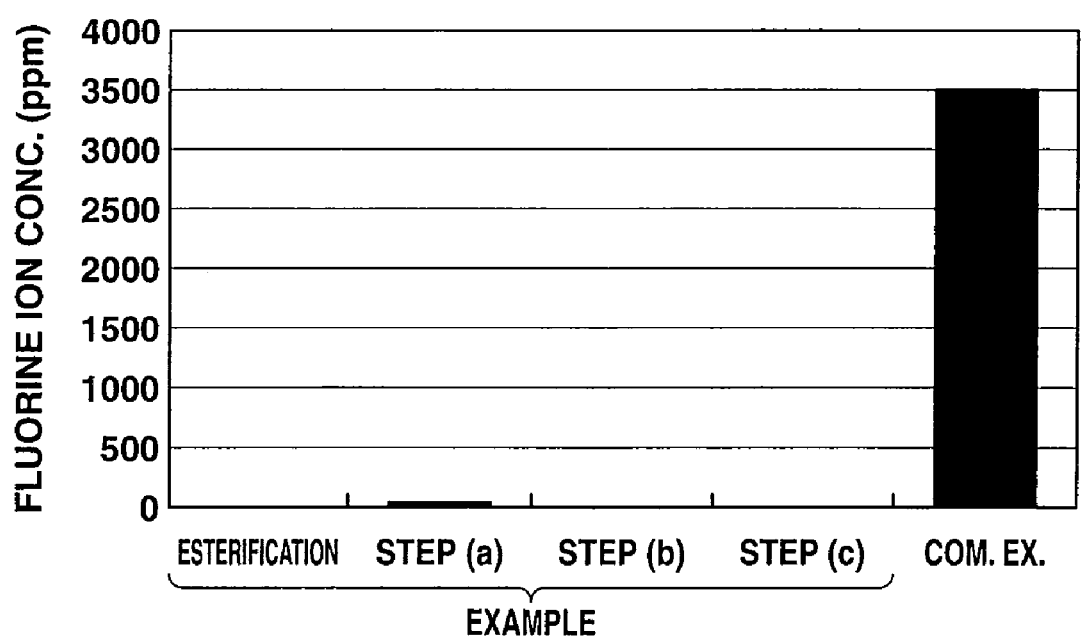

PROCESS FOR PRODUCING ALKOXYCARBONYLFLUOROALKANE SULFONATES

TECHNICAL FIELD

The present invention relates to a process for producing alkoxycarbonylfluoroalkanesulfonates, which are useful as photoacid generator and its intermediates. Photoacid generator is contained in a chemically amplified resist material, which is suitable for a micro-processing technology, particularly photolithography, in the production steps of semiconductor devices.

BACKGROUND OF THE INVENTION

In recent years, the trend toward micro-scale pattern rule has been increasing with the trend toward large-scale integration and high-speed LSI circuits. The trend toward a shorter wavelength of the exposure light source lies behind it. For example, it became possible to mass-produce 64M-bit (processing dimension: 0.25 μm or less) DRAM (dynamic random-access memory) by the wavelength shortening from mercury lamp i-line (365 nm) to KrF excimer laser (248 nm). Nowadays, a lithography using ArF excimer laser (193 nm) has increasingly been examined, and a 65 nm node device has been examined by a combination with a high NA lens (NA≧0.9). Although the use of $F_2$ laser (wavelength: 157 nm) had been named as a candidate for the production of the next 45 nm node devices, its application was postponed by many problems, such as cost increase of scanner, change of optical system, and low etching resistance of resist. As an alternative to $F_2$ lithography, proposed was ArF immersion lithography. Now, its development is going on toward an early introduction.

As a resist suitable for such exposure wavelength, "chemically amplified resist material" attracts much attention. This material contains a radiosensitive acid generator (hereinafter referred to as "photoacid generator"), which generates an acid by radiation irradiation (hereinafter, referred to as "exposure"). Furthermore, it is a pattern-forming material that forms a pattern by making a difference in solubility between the exposed portion and the unexposed portion through a reaction using the acid generated by the exposure as a catalyst.

Examples of the photoacid generator used for such chemically amplified resist material include onium sulfonates, such as iodonium sulfonate and sulfonium sulfonate, sulfonic acid esters, N-imidosulfonate, N-oximesulfonate, o-nitrobenzylsulfonate, and tris(methane)sulfonate of pyrogallol.

Examples of the acid generated from the photoacid generator upon exposure include alkanesulfonic acids, arylsulfonic acids, and partially or entirely fluorinated arylsulfonic acids and alkanesulfonic acids.

Of these, acid generators that generate partially or entirely fluorinated alkanesulfonic acids have a sufficient acid strength in deprotection reactions of protective groups that are difficult in deprotection, and therefore many of them have been put into practical use. Their examples include triphenylsulfonium trifluoromethanesulfonate and triphenylsulfonium perfluoro-n-octane sulfonate. Although triphenylsulfonium trifluoromethanesulfonate generates a sufficiently strong acid to have a sufficiently high-resolution performance, it has a defect of high mask dependency as a photoresist due to low boiling point of the acid and due to long diffusion length of the acid. Triphenylsulfonium perfluoro-n-octanesulfonate has a sufficient acidity and is almost appropriate in terms of acid boiling point and diffusion length. Therefore, it attracts much attention in recent years. However, it should be noted that perfluorooctyl sulfonates might be hazardous to human health and the environment (see "Perfluorooctyl Sulfonates; Proposed Significant New Use Rule" dated Oct. 18, 2000 (Volume 65, Number: 202) from the U.S. Environmental Protection Agency).

Under such background, there have been the developments of acid generators that generate partially or entirely fluorinated alkanesulfonic acids and that have characteristics of having a sufficient acidity, being appropriate in terms of acid boiling point and diffusion length, and having less load on the environment. Thus, there have been the developments of alkoxycarbonylfluoroalkanesulfonic acid onium salts as acid generators, such as triphenylsulfonium methoxycarbonyldifluoromethanesulfonate (see Japanese Patent Application Publication No. 2004-117959), (4-methylphenyl)diphenylsulfonyl t-butoxycarbonyldifluoromethane-sulfonate (see Japanese Patent Application Publication No. 2002-214774 corresponding to U.S. Patent Application Publication Nos. 2002/0102491, 2005/0130060 and 2007/0003871), and triphenylsulfonium (adamantane-1-ylmethyl)oxycarbonyldifluoromethanesulfonate (see Japanese Patent Application Publication No. 2004-4561 corresponding to US Patent Application Publication No. 2003/0194639).

The following reaction scheme [1] is known to obtain an alkoxycarbonylfluoroalkanesulfonic acid onium salt [vii] (see Japanese Patent Application Publication No. 2004-117959 and U.S. Pat. No. 2,852,554). In this reaction scheme, 3,3,4,4-tetrafluoro-[1,2]oxathiethane 2,2-dioxide [iii] is synthesized by reacting tetrafluoroethylene [i] with sulfur trioxide [ii]. Then, the compound [v] is synthesized by a ring-opening reaction of the compound [iii] using an alcohol (ROH). Alternatively, the compound [v] is synthesized by a two-step reaction, that is, a ring-opening isomerization of the compound [iii] to obtain an oxyfluoride [iv] and then an esterification of the oxyfluoride [iv] into the compound [v] by an alcohol (ROH). Then, the compound [v] is turned into a sulfonate (a sodium sulfonate) [vi] by an alkali metal containing base, followed by a salt exchange with an onium salt such as sulfonium salt ($Q^+X^-$ where $Q^+$ is a monovalent onium cation and $X^-$ is usually a halogen ion), thereby obtaining the target acid generator, an alkoxycarbonylfluoroalkanesulfonic acid onium salt [vii].

Reaction Scheme [1]

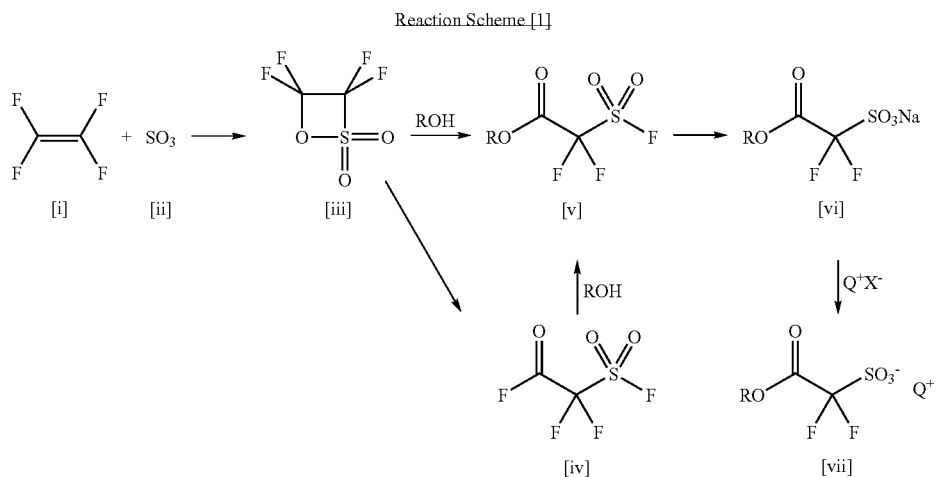

SUMMARY OF THE INVENTION

As shown in the reaction scheme [1], 3,3,4,4-tetrafluoro-[1,2]oxathiethane 2,2-dioxide [iii] used as a raw material for producing an alkoxycarbonylfluoroalkanesulfonate [vii] is synthesized from tetrafluoroethylene [i] and sulfur trioxide [ii]. Since this synthesis uses an explosive reagent, it is necessary to sufficiently pay attention to safety. Since it is a reaction with an industrially difficult skill, the resulting 3,3,4,4-tetrafluoro-[1,2]oxathiethane 2,2-dioxide [iii] inevitably has a very high price. Therefore, the reaction scheme [1] is not preferable for industrial use.

Furthermore, the reaction scheme [1] has a problem that hydrogen fluoride or fluoride is produced in a large amount by a conversion reaction of the oxyfluoride [iv] or [v]. In fact, hydrogen fluoride or fluorine ions that are separated from the fluoride corrode a glass reactor to have devitrification. Since a strong acid, hydrogen fluoride, is generated by the contact of the fluoride with acid, it is not possible to use a metal (e.g., iron or stainless steel) reactor in the reaction scheme. Thus, the material of the reactor usable in the reaction scheme [1] is considerably limited.

Since the conventional process for producing alkoxycarbonylfluoroalkane sulfonates has the above-mentioned several defects, there is a demand for a new industrial production process that can efficiently be conducted.

The present inventors have conducted an eager research to fulfill the above demand. As a result, we have found a novel process for easily producing an alkoxycarbonylfluoroalkanesulfonate by using a halofluoroalkanoate, which has a low price and is easily available, as a starting material. Since hydrogen fluoride or fluoride is not produced as a by-product in this novel process, the material of the reactor used therein is not limited.

That is, according to the present invention, there is provided a first process for producing an alkoxycarbonylfluoroalkanesulfonate represented by the formula [1]

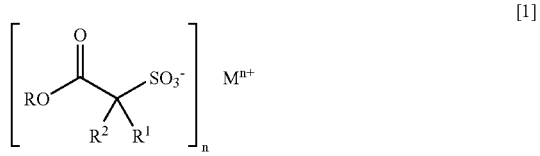

[1]

comprising the steps of:
(a) reacting a halofluoroalkanoate represented by the formula [2]

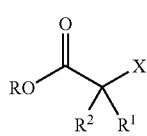

[2]

with a sulfinating agent, thereby obtaining an alkoxycarbonylfluoroalkanesulfinate represented by the formula [3]

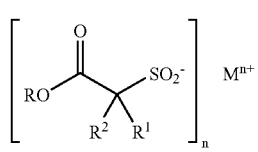

[3]

and
(b) reacting the alkoxycarbonylfluoroalkanesulfinate with an oxidizing agent, thereby obtaining the alkoxycarbonylfluoroalkanesulfonate represented by the formula [1],
wherein, in the formula [1], R represents a $C_1$-$C_{25}$ straight-chain, branched-chain or cyclic alkyl group, or a $C_2$-$C_{25}$ straight-chain, branched-chain or cyclic alkenyl group, where hydrogen atoms of the alkyl group may partially or entirely be replaced with fluorine or hydroxyl group, where two hydrogen atoms on a carbon atom of the alkyl group may be replaced with an oxygen atom to form a keto group, where hydrogen atoms of the alkenyl group may partially or entirely be replaced with fluorine or hydroxyl group, and where two hydrogen atoms on a methylene carbon atom of the alkenyl group may be replaced with an oxygen atom to form a keto group, wherein, in the formula [1], each of $R^1$ and $R^2$ independently represents a fluorine atom, or a $C_1$-$C_6$ straight-chain, branched-chain or cyclic perfluoroalkyl group, wherein, in the formula [1], $M^{n+}$ represents a counter cation, and n represents a positive integer, wherein, in the formula [2], X represents a chlorine atom, bromine atom or iodine atom; and R, $R^1$ and $R^2$ are defined as in the formula [1], wherein, in the formula [3], R, $R^1$, $R^2$, $M^{n+}$ and n are defined as in the formula [1].

According to the present invention, there is provided a second process for producing an alkoxycarbonylfluoroalkanesulfonic acid onium salt represented by the formula [4]

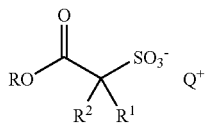

[4]

comprising the steps of:

(a) reacting a halofluoroalkanoate represented by the formula [2], with a sulfinating agent, thereby obtaining an alkoxycarbonylfluoroalkanesulfinate represented by the formula [3];

(b) reacting the alkoxycarbonylfluoroalkanesulfinate with an oxidizing agent, thereby obtaining an alkoxycarbonylfluoroalkanesulfonate represented by the formula [1]; and (c) reacting the alkoxycarbonylfluoroalkanesulfonate represented by the formula [1] with a monovalent onium salt represented by the formula [5]

Q⁺X⁻     [5]

to conduct a salt exchange, thereby obtaining the alkoxycarbonylfluoroalkanesulfonic acid onium salt represented by the formula [4], wherein, in the formula [4], R, $R^1$ and $R^2$ are defined as in the formula [1], wherein, in the formula [4], Q⁺ represents monovalent onium cation that is a sulfonium cation represented by the formula [6]

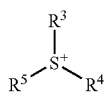

[6]

or an iodonium cation represented by the formula [7]

R⁶—I⁺—R⁷     [7]

wherein, in the formula [6], each of $R^3$, $R^4$ and $R^5$ independently represents a $C_1$-$C_{30}$ straight-chain or branched alkyl group optionally having a substituent; a $C_3$-$C_{30}$, cyclic, monovalent, hydrocarbon group optionally having a substituent; a $C_6$-$C_{30}$ aryl group optionally having a substituent; or an unsubstituted, monovalent, heterocyclic organic group having a number of atoms of 4-30, wherein, in the formula [6], at least two of $R^3$, $R^4$ and $R^5$ may be bonded to each other through sulfur atom of the formula [6] to form a ring, wherein, in the formula [7], each of $R^6$ and $R^7$ independently represents a $C_1$-$C_{30}$ straight-chain or branched alkyl group optionally having a substituent; a $C_3$-$C_{30}$, cyclic, monovalent, hydrocarbon group optionally having a substituent; a $C_6$-$C_{30}$ aryl group optionally having a substituent; or an unsubstituted, monovalent, heterocyclic organic group having a number of atoms of 4-30, wherein, in the formula [7], $R^6$ and $R^7$ may be bonded to each other through iodine atom of the formula [7] to form a ring, wherein, in the formula [5], Q⁺ is defined as in the formula [4], and X⁻ represents a monovalent anion.

According to the present invention, a halofluoroalkanoate represented by the formula [2], which is the starting material of the first and second processes, can be obtained by esterifying a halofluoroacetic acid derivative represented by the formula [8], the formula [9] or the formula [10]

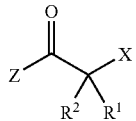

[8]

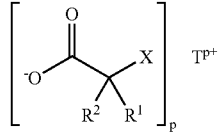

[9]

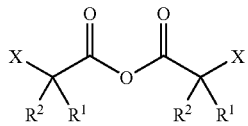

[10]

wherein, in the formula [8], Z represents a hydroxyl group, fluorine, chlorine, bromine or iodine; $R^1$ and $R^2$ are defined as in the formula [1]; and X is defined as in the formula [2], wherein, in the formula [9], $T^{p+}$ represents a corresponding metal cation, p represents a positive integer; $R^1$ and $R^2$ are defined as in the formula [1]; and X is defined as in the formula [2], wherein, in the formula [10], $R^1$ and $R^2$ are defined as in the formula [1]; and X is defined as in the formula [2].

The present invention has characteristics that all of the necessary raw materials have low prices, that the operations are easy, and that the reactor used is not limited.

BRIEF DESCRIPTION OF THE DRAWINGS

FIGURE is a graph showing fluorine concentrations in each step of Example and in Comparative Example.

DETAILED DESCRIPTION

As stated above, photoacid generator is contained in a chemically amplified resist material, which is suitable for a micro-processing technology, particularly photolithography, in the production steps of semiconductor devices. According to the present invention, it is possible to produce alkoxycarbonylfluoroalkanesulfonates, which are useful as such photoacid generator and its intermediates, by using a difluoroacetate as a raw material, which has low price and is easily available, under mild condition, with easy operations, with high yield, and with less wastes.

As shown in the following reaction scheme [2], an alkoxycarbonylfluoroalkanesulfonate represented by the formula [1], which is the target product of the first process of the present invention, can be produced by conducting the steps of:

(a) reacting a halofluoroalkanoate represented by the formula [2] with a sulfinating agent, thereby obtaining an alkoxycarbonylfluoroalkanesulfinate represented by the formula [3]; and (b) reacting the alkoxycarbonylfluoroalkanesulfinate with an oxidizing agent.

Furthermore, an alkoxycarbonylfluoroalkanesulfonic acid onium salt represented by the formula [4], which is the target product of the second process of the present invention, can be produced by conducing the step of (c) reacting the alkoxycarbonylfluoroalkanesulfonate represented by the formula [1] with a monovalent onium salt represented by the formula [5] to conduct a salt exchange.

Furthermore, the halofluoroalkanoate represented by the formula [2], which is the starting material of the first and second processes, can be prepared by esterifying a halofluoroacetic acid derivative represented by the formula [8], the formula [9] or the formula [10]

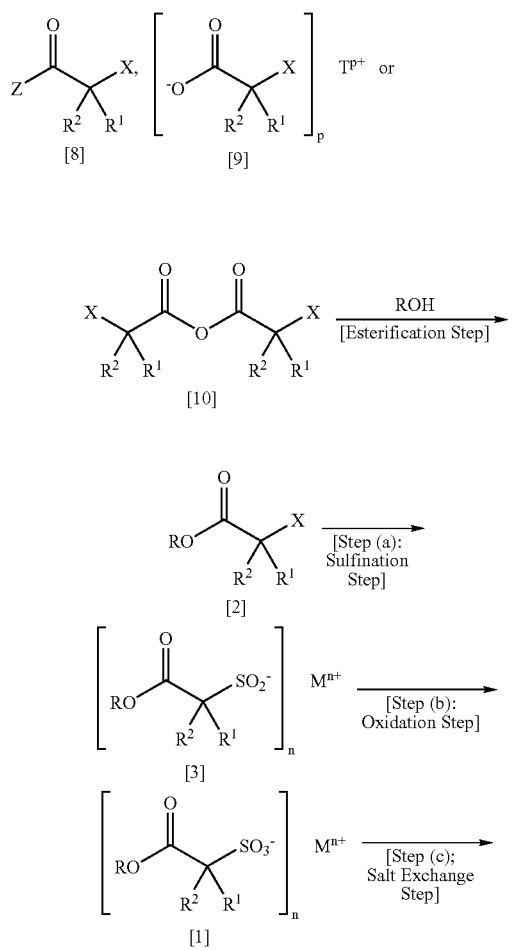

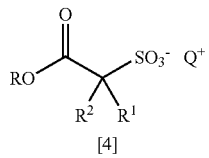

In the following, each step of the reaction scheme 2 is described in detail. At first, the esterification step for producing the halofluoroalkanoate represented by the formula [2], which is used in the step (a), is described. This esterification step is a step of reacting a carboxylic acid or carboxyhalide represented by the formula [8], a metal carboxylate represented by the formula [9], or a carboxylic anhydride represented by the formula [10], with an alcohol ROH.

Examples of the carboxylic acid or carboxyhalide represented by the formula [8] include chlorodifluoroacetic acid, bromodifluoroacetic acid, iododifluoroacetic acid, 2-chloro-2,3,3,3-tetrafluoropropanoic acid, 2-bromo-2,3,3,3-tetrafluoropropanoic acid, 2-iodo-2,3,3,3-tetrafluoropropanoic acid, 2-chloro-2-(trifluoromethyl)-3,3,3-trifluoropropanoic acid, 2-bromo-2-(trifluoromethyl)-3,3,3-trifluoropropanoic acid, 2-iodo-2-(trifluoromethyl)-3,3,3-trifluoropropanoic acid, chlorodifluoroacetic fluoride, bromodifluoroacetic fluoride, iododifluoroacetic fluoride, 2-chloro-2,3,3,3-tetrafluoropropanoic fluoride, 2-bromo-2,3,3,3-tetrafluoropropanoic fluoride, 2-iodo-2,3,3,3-tetrafluoropropanoic fluoride, 2-chloro-2-(trifluoromethyl)-3,3,3-trifluoropropanoic fluoride, 2-bromo-2-(trifluoromethyl)-3,3,3-trifluoropropanoic fluoride, 2-iodo-2-(trifluoromethyl)-3,3,3-trifluoropropanoic fluoride, chlorodifluoroacetic chloride, bromodifluoroacetic chloride, iododifluoroacetic chloride, 2-chloro-2,3,3,3-tetrafluoropropanoic chloride, 2-bromo-2,3,3,3-tetrafluoropropanoic chloride, 2-iodo-2,3,3,3-tetrafluoropropanoic chloride, 2-chloro-2-(trifluoromethyl)-3,3,3-trifluoropropanoic chloride, 2-bromo-2-(trifluoromethyl)-3,3,3-trifluoropropanoic chloride, 2-iodo-2-(trifluoromethyl)-3,3,3-trifluoropropanoic chloride, chlorodifluoroacetic bromide, bromodifluoroacetic bromide, iododifluoroacetic bromide, 2-chloro-2,3,3,3-tetrafluoropropanoic bromide, 2-bromo-2,3,3,3-tetrafluoropropanoic bromide, 2-iodo-2,3,3,3-tetrafluoropropanoic bromide, 2-chloro-2-(trifluoromethyl)-3,3,3-trifluoropropanoic bromide, 2-bromo-2-(trifluoromethyl)-3,3,3-trifluoropropanoic bromide, 2-iodo-2-(trifluoromethyl)-3,3,3-trifluoropropanoic bromide, chlorodifluoroacetic iodide, bromodifluoroacetic iodide, iododifluoroacetic iodide, 2-chloro-2,3,3,3-tetrafluoropropanoic iodide, 2-bromo-2,3,3,3-tetrafluoropropanoic iodide, 2-iodo-2,3,3,3-tetrafluoropropanoic iodide, 2-chloro-2-(trifluoromethyl)-3,3,3-trifluoropropanoic iodide, 2-bromo-2-(trifluoromethyl)-3,3,3-trifluoropropanoic iodide, and 2-iodo-2-(trifluoromethyl)-3,3,3-trifluoropropanoic iodide.

Examples of the metal carboxylate represented by the formula [9] include sodium chlorodifluoroacetate, sodium bromodifluoroacetate, sodium iododifluoroacetate, sodium 2-chloro-2,3,3,3-tetrafluoropropanoate, sodium 2-bromo-2,3,3,3-tetrafluoropropanoate, sodium 2-iodo-2,3,3,3-tetrafluoropropanoate, sodium 2-chloro-2-(trifluoromethyl)-3,3,3-trifluoropropanoate, sodium 2-bromo-2-(trifluoromethyl)-3,3,3-trifluoropropanoate, sodium 2-iodo- 2-(trifluoromethyl)-3,3,3-trifluoropropanoate, potassium chlorodifluoroacetate, potassium bromodifluoroacetate, potassium iododifluoroacetate, potassium 2-chloro-2,3,3,3-tetrafluoropropanoate, potassium 2-bromo-2,3,3,3-tetrafluoropropanoate, potassium 2-iodo-2,3,3,3-tetrafluoropropanoate, potassium 2-chloro-2-(trifluoromethyl)-3,3,3-trifluoropropanoate, potassium 2-bromo-2-(trifluoromethyl)-3,3,3-trifluoropropanoate, potassium 2-iodo-2-(trifluoromethyl)-3,3,3-trifluoropropanoate, calcium chlorodifluoroacetate, calcium bromodifluoroacetate, calcium iododifluoroacetate, calcium 2-chloro-2,3,3,3-tetrafluoropropanoate, calcium 2-bromo-2,3,3,3-tetrafluoropropanoate, calcium 2-iodo-2,3,3,3-tetrafluoropropanoate, calcium 2-chloro-2-(trifluoromethyl)-3,3,3-trifluoropropanoate, calcium 2-bromo-2-(trifluoromethyl)-3,3,3-trifluoropropanoate, calcium 2-iodo-2-(trifluoromethyl)-3,3,3-trifluoropropanoate, magnesium chlorodifluoroacetate, magnesium bromodifluoroacetate, magnesium iododifluoroacetate, magnesium 2-chloro-2,3,3,3-tetrafluoropropanoate, magnesium 2-bromo-2,3,3,3-tetrafluoropropanoate, magnesium 2-iodo-2,3,3,3-tetrafluoropropanoate, magnesium 2-chloro-2-(trifluoromethyl)-3,3,3-trifluoropropanoate, magnesium 2-bromo-2-(trifluoromethyl)-3,3,3-trifluoropropanoate, and magnesium 2-iodo-2-(trifluoromethyl)-3,3,3-trifluoropropanoate.

Examples of the carboxylic anhydride represented by the formula [10] include chlorodifluoroacetic anhydride, bromodifluoroacetic anhydride, iododifluoroacetic anhydride, 2-chloro-2,3,3,3-tetrafluoropropanoic anhydride, 2-bromo-2,3,3,3-tetrafluoropropanoic anhydride, 2-iodo-2,3,3,3-tetrafluoropropanoic anhydride, 2-chloro-2-(trifluoromethyl)-3,3,3-trifluoropropanoic anhydride, 2-bromo-2-(trifluoromethyl)-3,3,3-trifluoropropanoic anhydride, and 2-iodo-2-(trifluoromethyl)-3,3,3-trifluoropropanoic anhydride.

Of these, from the points of availability and low prices, preferable examples of the halofluoroacetic acid derivative represented by the formula [8], [9] or [10] are chlorodifluoroacetic acid, bromodifluoroacetic acid, 2-chloro-2,3,3,3-tetrafluoropropanoic acid, 2-bromo-2,3,3,3-tetrafluoropropanoic acid, chlorodifluoroacetic chloride, bromodifluoroacetic chloride, 2-chloro-2,3,3,3-tetrafluoropropanoic chloride, 2-bromo-2,3,3,3-tetrafluoropropanoic chloride, sodium chlorodifluoroacetate, sodium bromodifluoroacetate, sodium 2-chloro-2,3,3,3-tetrafluoropropanoate, sodium 2-bromo-2,3,3,3-tetrafluoropropanoate, potassium chlorodifluoroacetate, potassium bromodifluoroacetate, potassium 2-chloro-2,3,3,3-tetrafluoropropanoate, potassium 2-bromo-2,3,3,3-tetrafluoropropanoate, chlorodifluoroacetic anhydride, bromodifluoroacetic anhydride, 2-chloro-2,3,3,3-tetrafluoropropanoic anhydride, and 2-bromo-2,3,3,3-tetrafluoropropanoic anhydride.

Furthermore, from the viewpoint of reactivity, particularly preferable examples of the halofluoroacetic acid derivative are bromodifluoroacetic acid, 2-bromo-2,3,3,3-tetrafluoropropanoic acid, bromodifluoroacetic chloride, 2-bromo-2,3,3,3-tetrafluoropropanoic chloride, bromodifluoroacetic anhydride, and 2-bromo-2,3,3,3-tetrafluoropropanoic anhydride.

The above-mentioned compounds as the halofluoroacetic acid derivatives represented by the formulas [8], [9] and [10] are easy in availability and production of their starting materials, as compared with various sultones used in conventional processes. Therefore, it is possible to easily prepare those compounds with far lower prices, as compared with sultones. It may be one of the characteristics of the present invention that such compound can be used as the starting material.

In the alcohol ROH used in the esterification step, R is not particularly limited as long as it is a $C_1$-$C_{25}$ straight-chain, branched-chain or cyclic alkyl group, or a $C_2$-$C_{25}$ straight-chain, branched-chain or cyclic alkenyl group. Herein, hydrogen atoms of the alkyl group may partially or entirely be replaced with fluorine or hydroxyl group, two hydrogen atoms on a carbon atom of the alkyl group may be replaced with an oxygen atom to form a keto group, hydrogen atoms of the alkenyl group may partially or entirely be replaced with fluorine or hydroxyl group, and two hydrogen atoms on a methylene carbon atom of the alkenyl group may be replaced with an oxygen atom to form a keto group. Specific examples of this R include alkyl groups, such as methyl group, ethyl group, n-propyl group, i-propyl group, n-butyl group, 1-methylpropyl group, 2-methylpropyl group, t-butyl group, n-pentyl group, i-pentyl group, 1,1-dimethylpropyl group, 1-methylbutyl group, 1,1-dimethylbutyl group, n-hexyl group, n-heptyl group, i-hexyl group, n-octyl group, i-octyl group, 2-ethylhexyl group, n-nonyl group, n-decyl group, n-undecyl group, n-dodecyl group, cyclopropyl group, cyclopentyl group, cyclohexyl group, and 4-t-butylcyclohexyl group, cyclohexenyl group, a group containing a norbornene skeleton, a group containing a norbornane skeleton, a group containing an isobornyl skeleton, a group containing a tricyclodecane skeleton, a group containing a tetracyclododecane skeleton, and a group containing an adamantane skeleton.

A specific process of the esterification by reacting a carboxylic acid or carboxyhalide represented by the formula [8], a metal carboxylate represented by the formula [9], or a carboxylic anhydride represented by the formula [10], with an alcohol ROH is not particularly limited and can be any of conventional esterification processes.

In the following, the esterification by using the carboxyhalide or carboxylic anhydride is described in detail.

In the esterification, the amount of the carboxyhalide represented by the formula [8] or carboxylic anhydride represented by the formula [10] relative to the alcohol ROH is not particularly limited. It may be 0.1-5 moles, preferably 0.2-3 moles, more preferably 0.5-2 moles, particularly preferably 0.8-1.5 moles, per mol of the alcohol.

The reaction (esterification) may be conducted with no solvent or in a solvent inert to the reaction. Such solvent is not particularly limited, as long as it is inert to the reaction. The reaction may be conducted, for example, in water, organic solvent, or a mixed system of these. Examples of this organic solvent include hydrocarbons such as n-hexane, benzene, and toluene; ketones such as acetone, methyl ethyl ketone, and methyl isobutyl ketone; esters such as ethyl acetate and butyl acetate; ethers such as diethyl ether, diethylene glycol dimethyl ether, tetrahydrofuran, and dioxane; halogen-containing solvents such as dichloromethane, chloroform, carbon tetrachloride, 1,2-dichloroethane, tetrachloro ethylene, chlorobenzene, and ortho-chlorobenzene; and polar solvents such as acetonitrile, N,N-dimethylformamide, N,N-dimethylimidazolidinone, dimethylsulfoxide, and sulforane. These solvents may be used singly or in a combination of at least two.

The reaction temperature is not particularly limited. It may be in a range of −78 to 150° C., preferably −20 to 120° C., more preferably 0 to 100° C.

Although the reaction time is also dependent on the reaction temperature, it may be several minutes to 100 hours, preferably 30 minutes to 50 hours, more preferably 1 to 20 hours. It is also possible to terminate the reaction to have any conversion, while checking conversion by a known analytical means (e.g., liquid chromatography, gas chromatography, thin-layer chromatography, and IR).

The reaction may be conducted with no catalyst, while eliminating hydrogen halide produced as a by-product from the reaction system, or may be conducted by using a dehydrohalogenation agent.

Examples of the dehydrohalogenation agent include organic bases such as triethylamine, pyridine, picoline, dimethylaniline, diethylaniline, 1,4-diazabicyclo [2.2.2]octane (DABCO), 1,8-diazabicyclo [5.4.0] undec-7-ene; and inorganic bases such as sodium hydrogencarbonate, sodium carbonate, potassium carbonate, lithium carbonate, sodium hydroxide, potassium hydroxide, calcium hydroxide, and magnesium oxide.

The amount of the dehydrohalogenation agent used in the reaction is not particularly limited. It may be 0.05 to 10 moles, preferably 0.1 to 5 moles, more preferably 0.5 to 3 moles, per mol of the alcohol ROH.

The step (a) (sulfination step) is described in detail in the following. This step is conducted by reacting a halofluoroalkanoate represented by the formula [2], which can be obtained by the previous step (esterification step), with a sulfinating agent, thereby obtaining an alkoxycarbonylfluoroalkanesulfinate represented by the formula [3].

Examples of the sulfinating agent include lithium hydrosulfite, sodium hydrosulfite, potassium hydrosulfite, ammonium hydrosulfite, sodium hydroxymethanesulfinate, zinc hydroxymethanesulfinate, sodium sulfite, potassium sulfite, sodium hydrogensulfite, and potassium hydrogensulfite. Of these, sodium hydrosulfite and potassium hydrosulfite are preferable, and sodium hydrosulfite is particularly preferable. $M^{n+}$ in the formula [3] is a counter cation. Although this counter cation corresponds to various cation species existing in the system, it is derived mainly from the sulfinating agent. In case that, for example, sodium hydrosulfite is used as the sulfinating agent, the counter cation is mainly sodium ion.

The molar ratio of the sulfinating agent (e.g., sodium hydrosulfite) to the halofluoroalkanoate may be 0.5-10, preferably 0.9-5.0, particularly preferably 1.0-2.0.

Although the reaction can be conducted in the air, sodium hydrosulfite as the sulfinating agent may be decomposed in some cases by water vapor in the air. Therefore, it is preferable to conduct it in an atmosphere of nitrogen or argon.

The reaction can be accelerated by adding an inorganic base or organic base. Examples of the inorganic base include ammonia, lithium carbonate, sodium carbonate, potassium carbonate, lithium hydrogencarbonate, sodium hydrogencarbonate, and potassium hydrogencarbonate. Examples of the organic base include trimethylamine, diethylamine, triethylamine, n-propylamine, n-butylamine, tri-n-butylamine, diisopropylethylamine, and aniline. Of these, the inorganic base is preferable, since not only it has a greater reaction acceleration effect, but also it can easily be separated and removed after the termination of the following step (particularly the salt exchange reaction of the step (c)). Of the inorganic bases, sodium hydrogencarbonate and potassium hydrogencarbonate are particularly preferable.

The molar ratio of the inorganic base to the sulfinating agent (e.g., sodium hydrosulfite) may be 0.1-10.0, preferably 1.0-3.0.

In case that an inorganic base has been added as the reaction acceleration agent, a cation of this inorganic base also becomes the counter cation ($M^{n+}$) in the formula [3]. In particular, in case that the counter cation of the sulfinating agent is different from that of the inorganic base, the counter cation ($M^{n+}$) in the formula [3] will be one in which those cations derived from the sulfinating agent and the inorganic base are coexistent with each other.

It is preferable to conduct the reaction in a mixed solvent of an organic solvent and water. This organic solvent can be selected from solvents compatible with water, such as lower alcohols, tetrahydrofuran, N,N-dimethylformamide, N,N-dimethylacetamide, acetonitrile, and dimethylsulfoxide. Of these, acetonitrile is particularly preferable.

The amount of the organic solvent may be at least 5 parts by weight, preferably at least 10 parts by weight, more preferably 20 to 90 parts by weight, relative to 100 parts by weight of the total of the organic solvent and the water.

The reaction temperature may be 40 to 200° C., preferably 60 to 100° C. The reaction time may be 0.5 to 72 hours, preferably 2 to 24 hours. In case that the reaction temperature is higher than the boiling point of the organic solvent or water, the reaction can be conducted by using a pressure-proof container such as autoclave.

The step (b) (oxidation step) is described in detail in the following. This step is conducted by reacting the alkoxycarbonylfluoroalkanesulfinate [3], which has been obtained by the step (a), with an oxidizing agent, thereby obtaining an alkoxycarbonylfluoroalkanesulfonate represented by the formula [1].

Examples of the oxidizing agent include hydrogen peroxide, metachloroperbenzoic acid, t-butylhydroperoxide, potassium peroxysulfate, potassium permanganate, sodium perborate, sodium metaiodate, chromic acid, sodium dichromate, halogens, iodobenzene dichloride, iodobenzene diacetate, osmium (VIII) oxide, ruthenium (VIII) oxide, sodium hypochlorite, sodium chlorite, oxygen gas, and ozone gas. Of these, preferable ones are hydrogen peroxide, metachloroperbenzoic acid, and t-butylhydroperoxide.

The molar ratio of the oxidizing agent to the alkoxycarbonylfluoroalkanesulfinate [3] may be 0.9-10.0, preferably 1.0-2.0.

In the step (b), a transition metal catalyst can be used together with the oxidizing agent. Examples of this transition metal catalyst include disodium tungstate, iron (III) chloride, ruthenium (III) chloride, and selenium (IV) oxide. Of these, disodium tungstate is preferable.

The molar ratio of the transition metal catalyst to the alkoxycarbonylfluoroalkanesulfinate [3] may be 0.0001-1.0, preferably 0.001-0.5, more preferably 0.001-0.1.

In addition to the oxidizing agent and the transition metal catalyst, it is possible to use a buffer in the step (b) for the purpose of adjusting pH of the reaction liquid. Examples of the buffer include disodium hydrogenphosphate, sodium dihydrogenphosphate, dipotassium hydrogenphosphate, and potassium dihydrogenphosphate. The molar ratio of the buffer to the alkoxycarbonylfluoroalkanesulfinate [3] may be 0.01-2.0, preferably 0.03-1.0, more preferably 0.05-0.5.

The reaction of the step (b) is normally conducted in a reaction solvent. Examples of this reaction solvent include water and organic solvents such as lower alcohols, tetrahydrofuran, N,N-dimethylformamide, N,N-dimethylacetamide, acetonitrile, dimethylsulfoxide, acetic acid, and trifluoroacetic acid. More preferable examples are water, methanol, N,N-dimethylacetamide, acetonitrile, and dimethylsulfoxide. Particularly preferable examples are water and methanol.

According to need, it is possible to use an organic solvent and water together. In this case, the amount of the organic solvent may be 5 parts by weight or greater, preferably 10 parts by weight or greater, more preferably 20-90 parts by weight, relative to 100 parts by weight of the total of the organic solvent and water. The amount of the reaction solvent may be 5-100 parts by weight, preferably 10-100 parts by weight, more preferably 20-50 parts by weight, relative to 100 parts by weight of the alkoxycarbonylfluoroalkanesulfinate [3].

The reaction temperature may be 0-100° C., preferably 5-60° C., more preferably 5-40° C. The reaction time may be 0.1-72 hours, preferably 0.5-24 hours, more preferably 0.5-12 hours.

The step (c) (salt exchange step) is described in detail in the following. This step is conducted by reacting the alkoxycarbonylfluoroalkanesulfonate represented by the formula [1], which has been obtained by the step (b), with a monovalent onium salt $Q^+X^-$ to conduct a salt exchange (ion exchange), thereby obtaining the alkoxycarbonylfluoroalkanesulfonic acid onium salt represented by the formula [4].

The ion exchange of the alkoxycarbonylfluoroalkanesulfonate [1] can be conducted, for example, by a standard process described in "Advances in Polymer Science", Vol. 62, p. 1-48 or by the process of the after-mentioned Example.

As defined above, the monovalent onium cation ($Q^+$) of the monovalent onium salt $Q^+X^-$ is a sulfonium cation represented by the formula [6] or an iodonium cation represented by the formula [7].

Specific examples of the sulfonium cation include trimethylsulfonium ion, tributylsulfonium ion, dimethyl(2-oxocyclohexyl)sulfonium ion, bis(2-oxocyclohexyl)methylsulfonium ion, (10-camphenoyl)methyl(2-oxocyclohexyl)sulfonium ion, (2-norbornyl)methyl(2-oxocyclohexyl)sulfonium ion, triphenylsulfonium ion, diphenyltolylsulfonium ion, diphenylxylylsulfonium ion, mesityldiphenylsulfonium ion, (t-butylphenyl)diphenylsulfonium ion, (octylphenyl)diphenylsulfonium ion, (cyclohexylphenyl)diphenylsulfonium ion, biphenyldiphenylsulfonium ion, (hydroxymethylphenyl)diphenylsulfonium ion, (methoxymethylphenyl)diphenylsulfonium ion, (actylphenyl)diphenylsulfonium ion, (benzoylphenyl)diphenylsulfonium ion, (hydroxycarbonylphenyl)diphenylsulfonium ion, (methoxycarbonylphenyl)diphenylsulfonium ion, (trifluoromethylphenyl)diphenylsulfonium ion, (fluorophenyl)diphenylsulfonium ion, (chlorophenyl)diphenylsulfonium ion, (bromophenyl)diphenylsulfonium ion, (iodophenyl)diphenylsulfonium ion, pentafluorophenyldiphenylsulfonium ion, (hydroxyphenyl)diphenylsulfonium ion, (methoxyphenyl)diphenylsulfonium ion, (butoxyphenyl)diphenylsulfonium ion, (acetyloxyphenyl)diphenylsulfonium ion, (benzoyloxyphenyl)diphenylsulfonium ion, (dimethylcarbamoylphenyl)diphenylsulfonium ion, (acetylamidophenyl)diphenylsulfonium ion, phenylditolylsulfonium ion, phenyldixylylsulfonium ion, dimesitylphenylsulfonium ion, bis(t-butylphenyl)phenylsulfonium ion, bis(octylphenyl)phenylsulfonium ion, bis(cyclohexylphenyl)phenylsulfonium ion, dibiphenylphenylsulfonium ion, bis(hydroxymethylphenyl)phenylsulfonium ion, bis(methoxymethylphenyl)phenylsulfonium ion, bis(acetylphenyl)phenylsulfonium ion, bis(benzoylphenyl)phenylsulfonium ion, bis(hydroxycarbonylphenyl)phenylsulfonium ion, bis(methoxycarbonylphenyl)phenylsulfonium ion, bis(trifluoromethylphenyl)phenylsulfonium ion, bis(fluorophenyl)phenylsulfonium ion, bis(chlorophenyl)phenylsulfonium ion, bis(bromophenyl)phenylsulfonium ion, bis(iodophenyl)phenylsulfonium ion, dipentafluorophenylphenylsulfonium ion, bis(hydroxyphenyl)phenylsulfonium ion, bis(methoxyphenyl)phenylsulfonium ion, bis(butoxyphenyl)phenylsulfonium ion, bis(acetyloxyphenyl)phenylsulfonium ion, bis(benzoyloxyphenyl)phenylsulfonium ion, bis(dimethylcarbamoylphenyl)phenylsulfonium ion, bis(acetylamidophenyl)phenylsulfonium ion, tristolylsulfonium ion, trisxylylsulfonium ion, trismesitylphenylsulfonium ion, tris(t-butylphenyl)sulfonium ion, tris(octylphenyl)sulfonium ion, tris(cyclohexylphenyl)sulfonium ion, tribiphenylsulfonium ion, tris(hydroxymethylphenyl)sulfonium ion, tris(methoxymethylphenyl)sulfonium ion, tris(acetylphenyl)sulfonium ion, tris(benzoylphenyl)sulfonium ion, tris(hydroxycarbonylphenyl)sulfonium ion, tris(methoxycarbonylphenyl)sulfonium ion, tris(trifluoromethylphenyl)sulfonium ion, tris(fluorophenyl)sulfonium ion, tris(chlorophenyl)sulfonium ion, tris(bromophenyl)sulfonium ion, tris(iodophenyl)sulfonium ion, dipentafluorophenylsulfonium ion, tris(hydroxyphenyl)sulfonium ion, tris(methoxyphenyl)sulfonium ion, tris(butoxyphenyl)sulfonium ion, tris(acetyloxyphenyl)sulfonium ion, tris(benzoyloxyphenyl)sulfonium ion, tris(dimethylcarbamoylphenyl)sulfonium ion, tris(acetylamidophenyl)sulfonium ion, methyldiphenylsulfonium ion, ethyldiphenylsulfonium ion, butyldiphenylsulfonium ion, hexyldiphenylsulfonium ion, octyldiphenylsulfonium ion, cyclohexyldiphenylsulfonium ion, 2-oxocyclohexyldiphenylsulfonium ion, norbornyldiphenylsulfonium ion, camphenoyldiphenylsulfonium ion, pinanoyldiphenylsulfonium ion, naphthyldiphenylsulfonium ion, antranyldiphenylsulfonium ion, benzyldiphenylsulfonium ion, trifluoromethyldiphenylsulfonium ion, methoxycarbonylmethyldiphenylsulfonium ion, butoxycarbonylmethyldiphenylsulfonium ion, benzoylmethyldiphenylsulfonium ion, (methylthiophenyl)diphenylsulfonium ion, (phenylthiophenyl)diphenylsulfonium ion, (acetylphenylthiophenyl)diphenylsulfonium ion, dimethylphenylsulfonium ion, diethylphenylsulfonium ion, dibutylphenylsulfonium ion, dihexylphenylsulfonium ion, dioctylphenylsulfonium ion, dicyclohexylphenylsulfonium ion, bis(2-oxocyclohexyl)phenylsulfonium ion, dinorbornylphenylsulfonium ion, dicamphenoylphenylsulfonium ion, dipinanoylphenylsulfonium ion, dinaphthylphenylsulfonium ion, dibenzylphenylsulfonium ion, trifluoromethyldiphenylsulfonium ion, bis(methoxycarbonylmethyl)phenylsulfonium ion, bis(butoxycarbonylmethyl)phenylsulfonium ion, dibenzoylmethylphenylsulfonium ion, bis(methylthiophenyl)phenylsulfonium ion, bis(phenylthiophenyl)phenylsulfonium ion, bis(acetylphenylthiophenyl)phenylsulfonium ion, dimethyl(2-oxocyclohexyl)sulfonium ion, bis(2-oxocyclohexyl)methylsulfonium ion, (10-camphenoyl)methyl(2-oxocyclohexyl)sulfonium ion, (2-norbornyl)methyl(2-oxocyclohexyl)sulfonium ion, triethylsulfonium ion, dihexylmethylsulfonium ion, trioctylsulfonium ion, dicyclohexylethylsulfonium ion, methyltetrahydrothiophenium ion, and triphenyloxosulfonium ion.

Specific examples of the iodonium cation include diphenyliodonium ion, bis-(t-butylphenyl)iodonium cation, (methoxyphenyl)phenyliodonium ion, (butoxyphenyl)phenyliodonium ion, trifluoroethylphenyliodonium ion, and pentafluorophenylphenyliodonium ion.

Of the above onium cations, triphenylsulfonium ion and diphenyliodonium ion are preferable, and triphenylsulfonium ion is particularly preferable.

Examples of the monovalent anion $X^-$ of the monovalent onium salt $Q^+X^-$ include $F^-$, $Cl^-$, $Br^-$, $I^-$, $ClO_4^-$, $HSO_4^-$, $H_2PO_4^-$, $BF_4^-$, $PF_6^-$, $SbF_6^-$, aliphatic sulfonic acid anion, aromatic sulfonic acid anion, trifluoromethanesulfonic acid anion, fluorosulfonic acid anion, aliphatic carboxylic acid anion, aromatic carboxylic acid anion, fluorocarboxylic acid anion, and trifluoroacetic acid anion. Of these, preferable ones are $Cl^-$, $Br^-$, $HSO_4^-$, $BF_4^-$ and aliphatic sulfonic acid ion, and more preferable ones are $Cl^-$, $Br^-$ and $HSO_4^-$.

The molar ratio of the monovalent onium salt $Q^+X^-$ to the alkoxycarbonylfluoroalkanesulfonate [1] may be 0.5-10.0, preferably 0.8-2.0, more preferably 0.9-1.2.

The reaction of the step (c) is normally conducted in a reaction solvent. Examples of this reaction solvent include water and organic solvents such as lower alcohols, tetrahydrofuran, N,N-dimethylformamide, N,N-dimethylacetamide, acetonitrile, and dimethylsulfoxide. More preferable examples are water, methanol, N,N-dimethylacetamide, acetonitrile, and dimethylsulfoxide. A particularly preferable example is water.

According to need, it is possible to use an organic solvent and water together. In this case, the amount of the organic solvent may be 5 parts by weight or greater, preferably 10 parts by weight or greater, more preferably 20-90 parts by weight, relative to 100 parts by weight of the total of the organic solvent and water. The amount of the reaction solvent may be 5-100 parts by weight, preferably 10-100 parts by weight, more preferably 20-50 parts by weight, relative to 100 parts by weight of the monovalent onium salt.

The reaction temperature may be 0-80° C., preferably 5-30° C. The reaction time may be 10 minutes to 16 hours, preferably 30 minutes to 6 hours.

According to need, the resulting alkoxycarbonylfluoroalkanesulfonic acid onium salt [4] can be purified by extraction with an organic solvent. Preferable examples of this organic solvent include organic solvents immiscible with water, such as esters (e.g., ethyl acetate and n-butyl acetate), ethers (e.g., diethyl ether), and halogenated alkanes (e.g., methylene chloride and chloroform).

The following nonlimitative example is illustrative of the present invention.

EXAMPLE

Esterification Step (Process for Producing Adamantane-1-ylmethyl bromodifluoroacetate)

A 200 mL, three-necked flask was charged with 4.76 g (31.8 mmol, 1.11 equivalents) of 1-adamantane methanol and 55 g of diethyl ether, followed by stirring to obtain a suspension. Then, 6.15 g (28.6 mmol, 1.0 equivalent) of bromodifluoroacetic chloride were added thereto. The resulting suspension was cooled down to 0° C. by using an iced bath, followed by adding 5.78 g (57.2 mmol, 2.0 equivalents) of triethylamine in a slow dropwise manner. This reaction liquid was allowed to stand with stirring to reach room temperature, followed by stirring at room temperature for 1 hour. Then, 50 g of water were added to wash the reaction liquid. The resulting organic layer was washed with 50 g of saturated sodium hydrogencarbonate, 50 g of saturated brine, and 50 g of water in sequence. Then, it was dried with magnesium sulfate, followed by distilling the solvent off, thereby obtaining 8.78 g of the target adamantane-1-ylmethyl bromodifluoroacetate (yield: 95%, purity: 100%).

Fluorine ions ($F^-$) were not detected from the wastewater produced by the esterification step.

Step (a) (Sulfination Step)

(Process for Producing Sodium (adamantane-1-ylmethyl) oxycarbonyldifluoromethanesulfinate)

In a 200 mL, three-necked flask, 9.55 g (29.6 mmol, 1.0 equivalent) of adamantane-1-ylmethyl bromodifluoroacetate were dissolved in 40 g of acetonitrile, followed by adding 4.96 g (59.0 mmol, 2.0 equivalents) of sodium hydrogencarbonate and 7.72 g (44.3 mmol, 1.5 equivalents) of sodium hydrosulfite. Then, 40 g of water were added, followed by stirring. The atmosphere of the reaction system was replaced with nitrogen. The reaction liquid was heated to 50° C., followed by stirring for 8 hours. After the reaction, an organic layer was recovered from the reaction liquid, and the remaining aqueous layer was extracted with 50 g of acetonitrile. The resulting two organic layers were combined together, followed by distilling the solvent off. Then, 50 g of diisopropyl ether were added to the residue to obtain a suspension, followed by stirring at room temperature for 30 minutes. This suspension was filtered, followed by distilling the solvent out of the filtrate, thereby obtaining 12.4 g of a solid containing the target sodium (adamantane-1-ylmethyl)oxycarbonyldifluoromethanesulfinate. This solid was found by NMR to contain 6.36 g of sodium (adamantane-1-ylmethyl) oxycarbonyldifluoromethanesulfinate (yield: 65%).

Fluorine ions ($F^-$) were detected by a trace amount of 22 ppm from the above aqueous layer of the reaction liquid.

Step (b) (Oxidation Step)

(Process for Producing Sodium (adamantane-1-ylmethyl) oxycarbonyldifluoromethanesulfonate)

In a 200 mL, three-necked flask, 12.4 g of the solid obtained by the step (a), containing 6.36 g (19.3 mmol, 1.0 equivalent) of sodium (adamantane-1-ylmethyl)oxycarbonyldifluoromethanesulfinate, were dissolved in 120 mL of water, followed by adding 5.03 g (44.4 mmol, 2.3 equivalents) of 30% hydrogen peroxide and 15 mg (0.045 mmol, 0.0024 equivalents) of disodium tungstate (VI) dihydrate, followed by stirring at room temperature for 1.5 hours. Then, water was distilled out of the reaction liquid, followed by drying, thereby obtaining 9.84 g of a solid containing the target sodium (adamantane-1-ylmethyl) oxycarbonyldifluoromethanesulfonate. This solid was found by NMR to contain 6.49 g of sodium (adamantane-1-ylmethyl) oxycarbonyldifluoromethanesulfonate (yield: 97%).

Fluorine ions ($F^-$) were not detected from the wastewater produced by the step (b).

Step (c) (Salt Exchange Step)

(Process for Producing Triphenylsulfonium (adamantane-1-ylmethyl)oxycarbonyldifluoromethanesulfonate)

In a 200 mL, three-necked flask, 8.86 g of the solid obtained by the step (b), containing 5.85 g (16.9 mmol, 1.0 equivalent) of sodium (adamantane-1-ylmethyl)oxycarbonyldifluoromethanesulfonate, were added to 83 g of water, followed by stirring to obtain a suspension and then heating to 80° C. At this temperature, it turned into a homogeneous solution. Then, an aqueous solution formed of 5.51 g (18.43 mmol, 1.1 equivalents) of triphenylsulfonium chloride and 60 g of water was added. Immediately after that, a white-color solid was precipitated. This solid was separated by filtration and then washed by pouring 50 g of water of 80° C. and 30 g of diisopropyl ether, thereby obtaining 9.91 g of the target triphenylsulfonium (adamantane-1-ylmethyl)oxycarbonyldifluoromethanesulfonate (yield: 100%, purity: 97%). Fluorine ions ($F^-$) were not detected from the wastewater produced by the step (c).

COMPARATIVE EXAMPLE

Process for Producing Sodium Methoxycarbonyldifluoromethanesulfonate

In a 2 L, three-necked, glass flask, 25.2 g (300 mmol, 3.0 equivalents) of sodium hydrogencarbonate were dissolved in 500 g of water, followed by adding 19.2 g (100 mmol, 1.0 equivalent) of methyl 2-(fluorosulfonyl)difluoroacetate in a dropwise manner at room temperature and stirring still at room temperature for 2 hours. Then, water was distilled out, thereby obtaining 46.5 g of a solid containing the target sodium methoxycarbonyldifluoromethanesulfonate.

As shown in Figure, fluorine ions (F⁻) were detected by 3500 ppm from the reaction liquid (aqueous solution) after the reaction. Since water was distilled out of this reaction liquid contained in the glass flask, the glass flask devitrified to have a white color.

What is claimed is:

1. A process for producing an alkoxycarbonylfluoroalkanesulfonate represented by the formula [1]

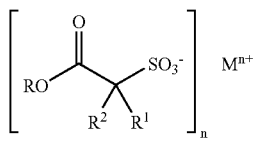
[1]

comprising the steps of:
(a) reacting a halofluoroalkanoate represented by the formula [2]

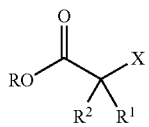
[2]

with a sulfinating agent, thereby obtaining an alkoxycarbonylfluoroalkanesulfinate represented by the formula [3]

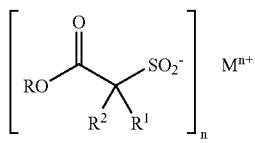
[3]

and
(b) reacting the alkoxycarbonylfluoroalkanesulfinate with an oxidizing agent, thereby obtaining the alkoxycarbonylfluoroalkanesulfonate represented by the formula [1], wherein, in the formula [1], R represents a $C_1$-$C_{25}$ straight-chain, branched-chain or cyclic alkyl group, or a $C_2$-$C_{25}$ straight-chain, branched-chain or cyclic alkenyl group, where hydrogen atoms of the alkyl group may partially or entirely be replaced with fluorine or hydroxyl group, where two hydrogen atoms on a carbon atom of the alkyl group may be replaced with an oxygen atom to form a keto group, where hydrogen atoms of the alkenyl group may partially or entirely be replaced with fluorine or hydroxyl group, and where two hydrogen atoms on a methylene carbon atom of the alkenyl group may be replaced with an oxygen atom to form a keto group, wherein, in the formula [1], each of $R^1$ and $R^2$ independently represents a fluorine atom, or a $C_1$-$C_6$ straight-chain, branched-chain or cyclic perfluoroalkyl group, wherein, in the formula [1], $M^{n+}$ represents a counter cation, and n represents a positive integer, wherein, in the formula [2], X represents a chlorine atom, bromine atom or iodine atom; and R, $R^1$ and $R^2$ are defined as in the formula [1], wherein, in the formula [3], R, $R^1$, $R^2$, $M^{n+}$ and n are defined as in the formula [1].

2. A process for producing an alkoxycarbonylfluoroalkanesulfonic acid onium salt represented by the formula [4]

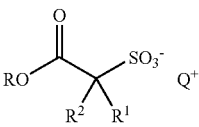
[4]

comprising the steps of:
(a) reacting a halofluoroalkanoate represented by the formula [2]

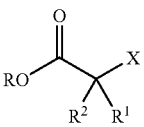
[2]

with a sulfinating agent, thereby obtaining an alkoxycarbonylfluoroalkanesulfinate represented by the formula [3]

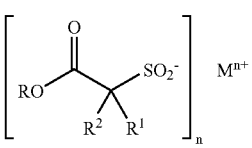
[3]

(b) reacting the alkoxycarbonylfluoroalkanesulfinate with an oxidizing agent, thereby obtaining an alkoxycarbonylfluoroalkanesulfonate represented by the formula [1]

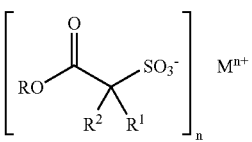
[1]

and
(c) reacting the alkoxycarbonylfluoroalkanesulfonate represented by the formula [1] with a monovalent onium salt represented by the formula [5]

$$Q^+X^- \qquad [5]$$

to conduct a salt exchange, thereby obtaining the alkoxycarbonylfluoroalkanesulfonic acid onium salt represented by the formula [4], wherein, in the formula [4], R represents a $C_1$-$C_{25}$ straight-chain, branched-chain or cyclic alkyl group, or a $C_2$-$C_{25}$ straight-chain, branched-chain or cyclic alkenyl group, where hydrogen atoms of the alkyl group may partially or entirely be replaced with fluorine or hydroxyl group, where two hydrogen atoms on a carbon atom of the alkyl group may be replaced with an oxygen atom to form a keto group, where hydrogen atoms of the alkenyl group may partially or entirely be replaced with fluorine or hydroxyl group, and where two hydrogen atoms on a methylene carbon atom of the alkenyl group may be replaced with an oxygen atom to form a keto group, wherein, in the formula [4], each of $R^1$ and $R^2$ independently represents a fluorine atom, or a $C_1$-$C_6$ straight-chain, branched-chain or cyclic perfluoroalkyl group, wherein, in the formula [4], $Q^+$ represents a monovalent onium cation that is a sulfonium cation represented by the formula [6]

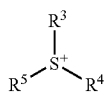

[6]

or an iodonium cation represented by the formula [7]

$R^6$—$I^+$—$R^7$ [7]

wherein, in the formula [6], each of $R^3$, $R^4$ and $R^5$ independently represents a $C_1$-$C_{30}$ straight-chain or branched alkyl group optionally having a substituent; a $C_3$-$C_{30}$, cyclic, monovalent, hydrocarbon group optionally having a substituent; a $C_6$-$C_{30}$ aryl group optionally having a substituent; or an unsubstituted, monovalent, heterocyclic organic group having a number of atoms of 4-30, wherein, in the formula [6], at least two of $R^3$, $R^4$ and $R^5$ may be bonded to each other through sulfur atom of the formula [6] to form a ring, wherein, in the formula [7], each of $R^6$ and $R^7$ independently represents a $C_1$-$C_{30}$ straight-chain or branched alkyl group optionally having a substituent; a $C_3$-$C_{30}$, cyclic, monovalent, hydrocarbon group optionally having a substituent; a $C_6$-$C_{30}$ aryl group optionally having a substituent; or an unsubstituted, monovalent, heterocyclic organic group having a number of atoms of 4-30, wherein, in the formula [7], $R^6$ and $R^7$ may be bonded to each other through iodine atom of the formula [7] to form a ring, wherein, in the formula [2], X represents a chlorine atom, bromine atom or iodine atom; and R, $R^1$ and $R^2$ are defined as in the formula [4], wherein, in the formula [3], $M^{n+}$ represents a counter cation, and n represents a positive integer, wherein, in the formula [3], R, $R^1$, and $R^2$ are defined as in the formula [4], wherein, in the formula [1], R, $R^1$, and $R^2$ are defined as in the formula [4], wherein, in the formula [1], $M^{n+}$ and n are defined as in the formula [3], wherein, in the formula [5], $Q^+$ is defined as in the formula [4], and $X^-$ represents a monovalent anion.

3. A process according to claim 1, further comprising, prior to the step (a), the step of esterifying a halofluoroacetic acid derivative represented by the formula [8], the formula [9] or the formula [10]

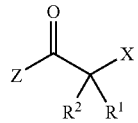

[8]

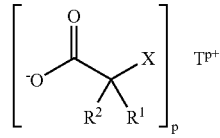

[9]

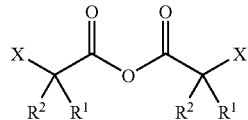

[10]

wherein, in the formula [8], Z represents a hydroxyl group, fluorine, chlorine, bromine or iodine; $R^1$ and $R^2$ are defined as in the formula [1]; and X is defined as in the formula [2], wherein, in the formula [9], $T^{p+}$ represents a corresponding metal cation, p represents a positive integer; $R^1$ and $R^2$ are defined as in the formula [1]; and X is defined as in the formula [2], wherein, in the formula [10], $R^1$ and $R^2$ are defined as in the formula [1]; and X is defined as in the formula [2].

4. A process according to claim 3, wherein the halofluoroacetic acid derivative is one selected from the group consisting of bromodifluoroacetic acid, 2-bromo-2,3,3,3-tetrafluoropropanoic acid, bromodifluoroacetic chloride, 2-bromo-2,3,3,3-tetrafluoropropanoic chloride, bromodifluoroacetic anhydride, and 2-bromo-2,3,3,3-tetrafluoropropanoic anhydride.

5. A process according to claim 1, wherein the sulfinating agent of the step (a) is sodium hydrosulfite.

6. A process according to claim 5, wherein the step (a) is conducted in an atmosphere of nitrogen or argon to prevent decomposition of the sodium hydrosulfite.

7. A process according to claim 1, wherein the step (a) is conducted in the presence of an inorganic base.

8. A process according to claim 7, wherein the inorganic base is sodium hydrogencarbonate or potassium hydrogencarbonate.

9. A process according to claim 1, wherein the step (a) is conducted in a mixed solvent that is a mixture of water and an organic solvent compatible with water.

10. A process according to claim 9, wherein the organic solvent is acetonitrile.

11. A process according to claim 1, wherein the oxidizing agent of the step (b) is hydrogen peroxide, metachloroperbenzoic acid, or t-butylhydroperoxide.

12. A process according to claim 1, wherein the step (b) is conducted in the presence of a transition metal catalyst.

13. A process according to claim 12, wherein the transition metal catalyst is disodium tungstate.

14. A process according to claim 1, wherein the halofluoroalkanoate represented by the formula [2] is adamantane-1-ylmethyl bromodifluoroacetate, wherein the alkoxycarbonylfluoroalkanesulfinate represented by the formula [3] is sodium (adamantane-1-ylmethyl) oxycarbonyldifluoromethanesulfinate, and wherein the alkoxycarbonylfluoroalkanesulfonate represented by the formula [1] is sodium (adamantane-1-ylmethyl)oxycarbonyldifluoromethanesulfonate.

15. A process according to claim 2, wherein $Q^+$ of the monovalent onium salt represented by the formula [5] is a triphenylsulfonium ion.

16. A process according to claim 2, wherein $X^-$ of the monovalent onium salt represented by the formula [5] is $Cl^-$, $Br^-$ or $HSO_4^-$.

17. A process according to claim 2, wherein the monovalent onium salt represented by the formula [5] is triphenylsulfonium chloride.

18. A process according to claim 2, wherein the halofluoroalkanoate represented by the formula [2] is adamantane-1-ylmethyl bromodifluoroacetate, wherein the alkoxycarbonylfluoroalkanesulfinate represented by the formula [3] is sodium (adamantane-1-ylmethyl) oxycarbonyldifluoromethanesulfinate, wherein the alkoxycarbonylfluoroalkanesulfonate represented by the formula [1] is sodium (adamantane-1-ylmethyl)oxycarbonyldifluoromethanesulfonate, and wherein the alkoxycarbonylfluoroalkanesulfonic acid onium salt represented by the formula [4] is triphenylsulfonium (adamantane-1-ylmethyl) oxycarbonyldifluoromethanesulfonate.

* * * * *